United States Patent [19]
Hammons

[11] Patent Number: 5,351,699
[45] Date of Patent: Oct. 4, 1994

[54] MALE CONDOM

[76] Inventor: Sharon Hammons, 4411 E. Woodrow Pl., Tulsa, Okla. 74115-4123

[21] Appl. No.: 130,263

[22] Filed: Oct. 1, 1993

[51] Int. Cl.⁵ .............................................. A61F 5/44
[52] U.S. Cl. .................................... 128/844; 128/918
[58] Field of Search ........................ 128/842, 844, 918

[56] References Cited

U.S. PATENT DOCUMENTS

| | | | |
|---|---|---|---|
| 3,759,254 | 9/1973 | Clark | 128/844 X |
| 4,834,113 | 5/1989 | Reddy | 128/844 X |
| 4,875,491 | 10/1989 | Parrone | 128/844 |
| 4,898,184 | 2/1990 | Skurkovich et al. | 128/844 |
| 4,920,983 | 5/1990 | Jimenez | 128/844 |
| 4,942,885 | 7/1990 | Davis et al. | 128/844 |
| 4,966,594 | 10/1990 | Thomas | 604/349 |
| 4,981,147 | 1/1991 | Barnett | 128/844 |
| 5,070,890 | 12/1991 | Papurt | 128/844 |

FOREIGN PATENT DOCUMENTS 429144  5/1991  European Pat. Off. ............ 128/844

*Primary Examiner*—Steven A. Bratlie
*Attorney, Agent, or Firm*—Catalano, Zingerman & McKay

[57] ABSTRACT

The present invention relates to a condom for use by a male user. The condom consists of a liquid impervious protective section for preventing exchange of body fluids between the user and a sexual partner during intercourse and a belt section for holding the condom on the user. The protection section is comprised of a tubular sheath portion which attaches to a bag portion into which the penis and the scrotum of the user are inserted, respectively, via an upwardly oriented opening in the bag portion. The opening is provided with an elasticized peripheral edge. A second protective layer is attached to the tubular sheath portion in order to help prevent the condom from breaking.

The belt section consists of a waistband with two leg straps. A front area of the waistband secures, either permanently or removably, to an anterior area of the peripheral edge of the opening in the bag portion. The two leg straps are each secured by one of their two ends to a back area of the waistband so that the leg straps are spaced apart on the waistband. The leg straps are secured, either permanently or removably, by their other ends to a posterior area of the peripheral edge of the opening in the bag portion.

7 Claims, 2 Drawing Sheets

MALE CONDOM

BACKGROUND OF THE INVENTION

1. Field of the Invention

The present invention relates to a condom for use by a male human being. More specifically, the present invention relates to a condom which provides protective coverage for both the penis and the scrotum of the user and secures to the user by means of a special belt.

2. Description of the Related Art

Concerns regarding sexually transmitted diseases, such as AIDs, has caused an increase recently in the use of condoms. The most common condoms are the sheath-type condoms which are designed to provide protective covering for only the penis. These sheath-type condoms are presently available over the counter at most drug stores.

One problem with these sheath-type condoms is that they tend to work off of the penis when the user in engaged in sexual intercourse, thus defeating the purpose of wearing the condom.

Another problem with these sheath-type condoms is that they often break during intercourse. Breakage is normally due to the tensional stress experienced by the condoms during intercourse.

A final problem with sheath-type condoms is that they do not provide coverage to the scrotum area, and therefore, do not provide complete coverage to the genital area of the user.

The present invention addresses these problems by providing a condom which covers both the penis and the scrotum of the user, which secures to the user by means of a special belt so that the condom will not work its way off of the user during intercourse, and which is provided with an additional layer of protective material near the proximal end of the sheath covering the penis in order to help prevent the condom from breaking during use.

SUMMARY OF THE INVENTION

The present invention relates to a condom which is comprised of a protective section and a special belt section. The protective section is provided with a hollow tubular sheath portion sealed at a distal end and attached at a proximal end to an anterior side of a hollow bag portion so that there is communication between the hollow tubular sheath and the hollow bag portion. The bag portion is provided with an opening with an elasticized peripheral edge. A second protective layer is provided external to the hollow tubular sheath portion. The second protective layer is in the form of a tube-shaped sleeve having a first open end and an opposite second end. The second end is turned inward to form a backward lip which secures to the external surface of the tubular sheath portion midway between the distal and proximal ends, with the first end being free to glide along the external surface of the tubular sheath portion. The belt section is comprised of a waistband and two leg straps. Each leg strap has a back end and a front end. The back end of each leg strap is secured to a back area of the waistband so that the back ends are spaced apart. The front ends of the leg straps secure, either permanently or detachably, to a posterior area provided on the peripheral edge of the opening of the bag portion. An anterior area provided on the peripheral edge of the opening secures, either permanently or detachably. to the front area of the waistband.

DETAILED DESCRIPTION OF THE PREFERRED EMBODIMENT

Figure 1:
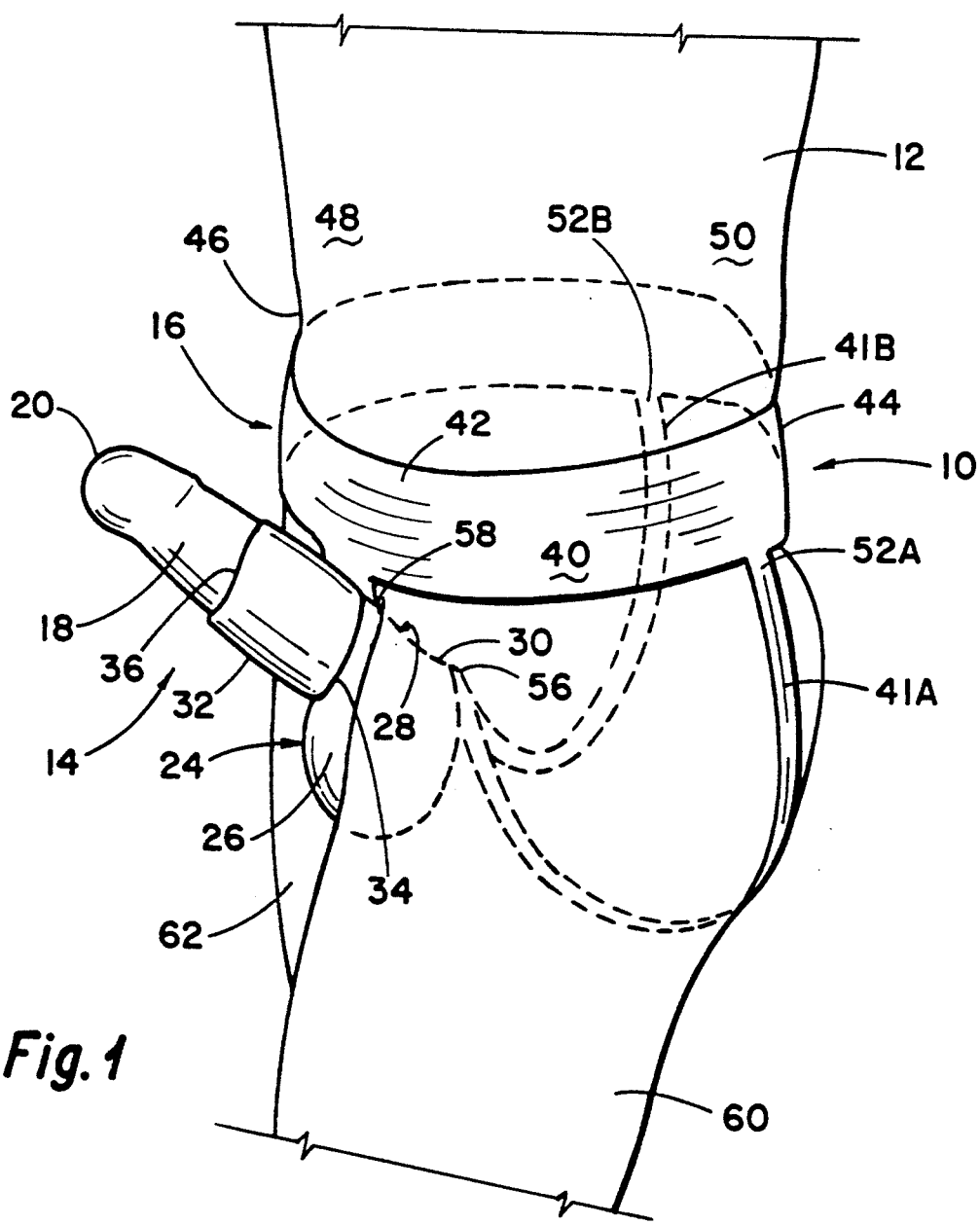
FIG. 1 shows a condom constructed according to a preferred embodiment of the present invention as the condom would appear when being worn by a user.

Referring now to the drawings and specifically to FIG. 1, there is illustrated a condom 10 constructed according to a preferred embodiment of the present invention. FIG. 1 shows the condom 10 being worn by a male user 12.

Figure 2:
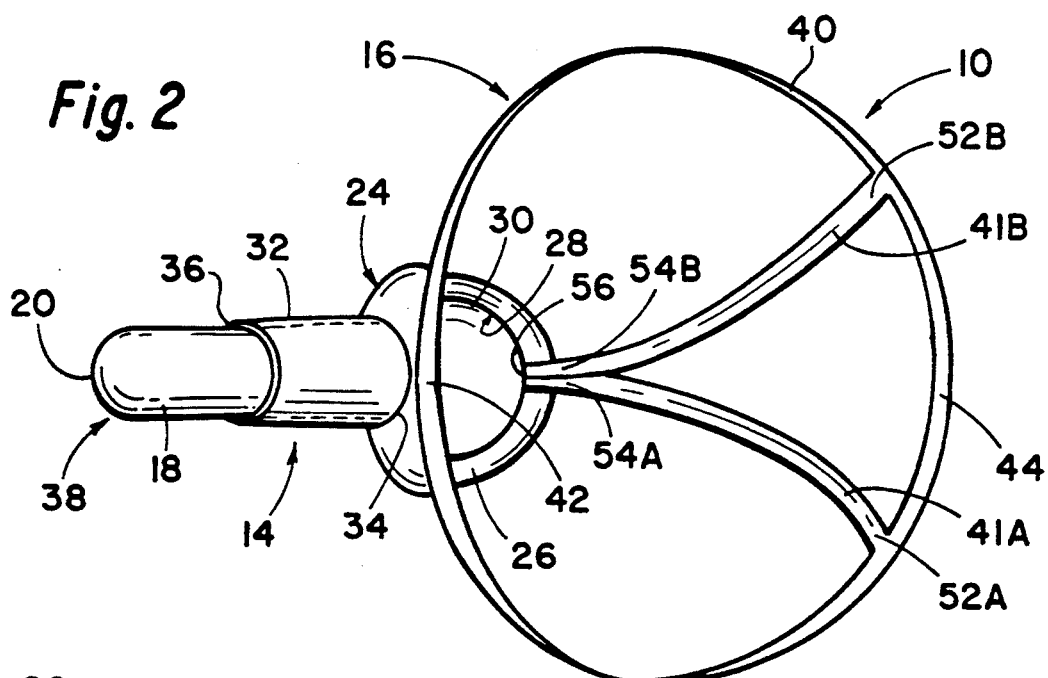
FIG. 2 is a top plan view of the condom of FIG. 1 removed from the user.
Figure 3:
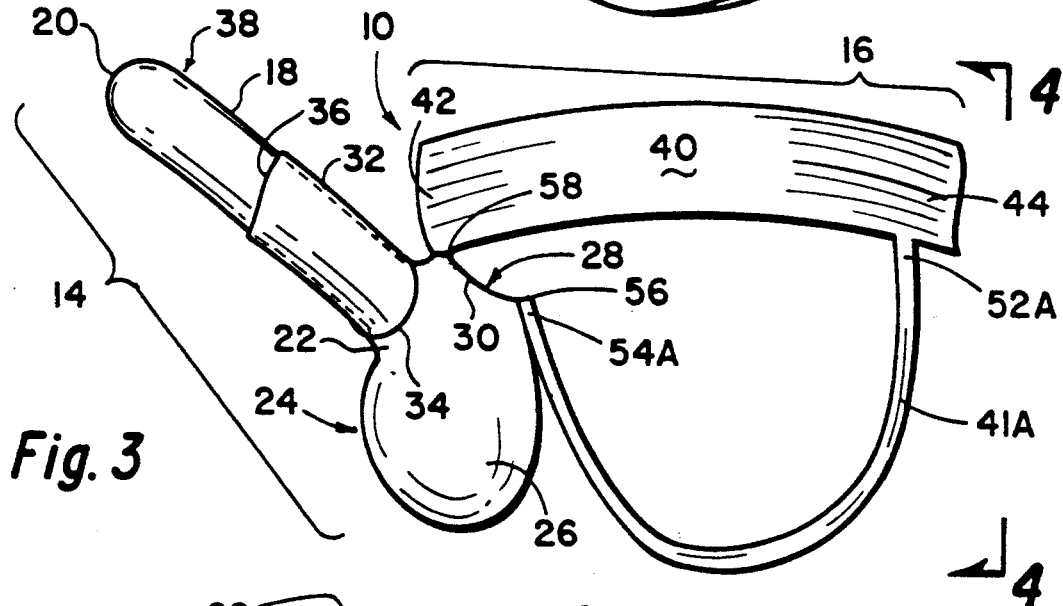
FIG. 3 is a left side elevation of the condom of FIG. 2.
Figure 4:
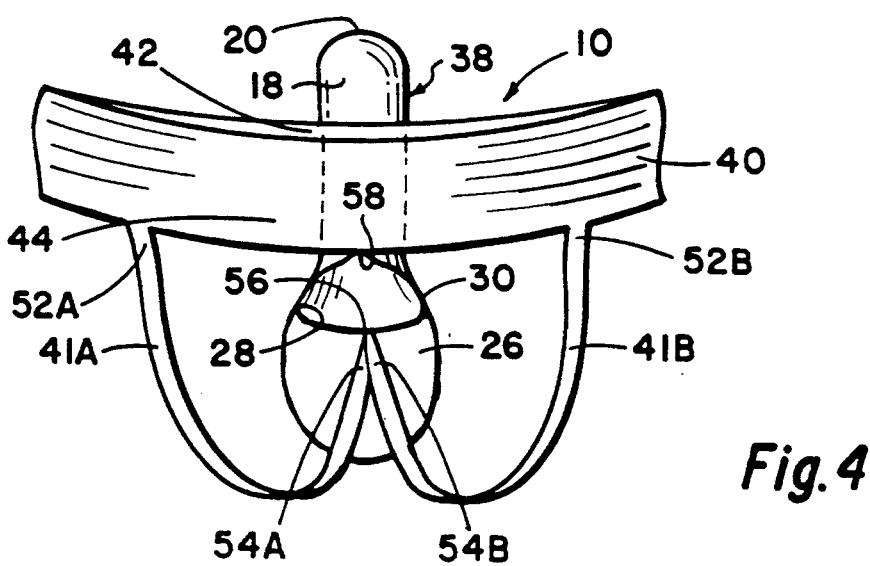
FIG. 4 is a view taken along line 4—4 of FIG. 3.

As illustrated in FIG. 3, the condom 10 is comprised of two components:

a protective section 14 and a special belt section 16. Referring now to FIGS. 2 through 4, the protective section 14 is comprised of a hollow tubular sheath portion 18 and a hollow bag portion 26. The hollow tubular sheath portion 18 is sealed on a distal end 20. An opposite proximal end 22 of the tubular sheath 18 attaches to an anterior side 24 of the hollow bag portion 26 so that the hollow tubular sheath 18 communicates with the hollow bag portion 26.

The bag portion 26 is provided with a single upwardly oriented opening 28. The opening 28 is provided circumferentially with an elasticized peripheral edge 30. When the user 12 puts on the condom 10, the user's penis (not illustrated) inserts first through the opening 28, then through the proximal end 22 of the tubular sheath portion 18 until it finally extends fully into the tubular sheath portion 18. Simultaneous with insertion of the penis (not illustrated) into the tubular sheath portion 18, the user's scrotum (not illustrated) inserts through the opening 28 so that the scrotum (not illustrated) extends into and is surrounded by the bag portion 26. The peripheral edge 30 of the opening 28 is elasticized so that the opening 28 can be expanded by stretching the peripheral edge 30 in order to admit the scrotum (not illustrated) and once the scrotum is within the bag portion 30, the peripheral edge 30 is released, thus allowing the peripheral edge 30 to return to its original contracted configuration in order to help to secure the bag portion 26 to the scrotum (not illustrated).

The entire protective section 14 preferably is constructed of a liquid impervious, flexible material such as latex, rubber or other suitable material in order to prevent exchange of body fluids between a sexual partner (not shown) and the user 12 when the user 12 is wearing the condom 10 during sexual intercourse.

Figure 5:
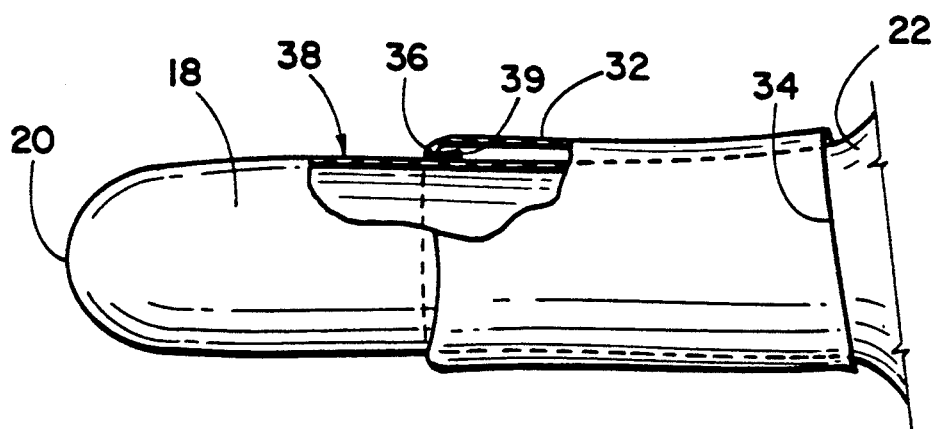
FIG. 5 is an enlarged partially cut-away view of the tubular sheath portion of the condom, showing details of the second protective layer.

As illustrated in FIG. 5, the tubular sheath portion 18 is provided with a second protective layer 32 which attaches circumferentially to the tubular sheath portion 18, approximately midway between the distal end 20 and the proximal end 22. The second protective layer 32 is a tube-shaped sleeve which is open on a first end 34 and secures on an opposite second end 36 to an external surface 38 provided on the tubular sheath portion 18. The second end 36 is turned inwardly into itself to form a backward oriented lip 39 within the second protective layer 32. The lip 39 is secured to the external surface 38 forming a continuous seal with the external surface 38 around the tubular sheath portion 18.

The first end 34 of the second protective layer 32 lays adjacent to the proximal end 22 of the tubular sheath portion 18, but does not attach thereto. The first end 34 is therefore free to move along the tubular sheath portion 18. In use, the second protective layer 32 tends to glide along the external surface 38 of the tubular sheath portion 18, thus reducing the tensional stress experienced by the tubular sheath portion 18 during intercourse and thereby reducing the possibility of the condom 10 breaking. The second protective layer 32 also serves as an apron for the tubular sheath portion 18 and helps to contain any body fluids located on the external surface 38.

The belt section 16 is comprised of a waistband 40 and two leg straps 41-A and 41-B. The waistband 40 is provided with a front area 42 and an opposite back area 44. As illustrated in FIG. 1, when the condom 10 is worn by the user 12, the waistband 40 encircles a waist 46 of the user 12 so that the front area 42 ties adjacent a tummy 48 of the user 12 and the back area 44 lies adjacent a lower back 50 of the user 12.

Each of the two leg straps 41-A and 41-B has a back end, 52-A and 52-B respectively, and a front end, 54-A and 54-B respectively. The back ends 52-A and 52-B each attach to the back area 44 of the waistband 40, with the back ends 52-A and 52-B spaced apart on the waistband 40. The waistband 40 and the leg straps 41-A and 41-B are preferably elasticized so that the belt section 16 snugs to the user 12 when the condom 10 is being worn.

The front ends 54-A and 54-B each attach to a posterior area 56 provided on the peripheral edge 30 of the opening 28. An anterior portion 58 provided on the peripheral edge 30 of the opening 28 secures to the front area 42 of the waistband 40.

In order to put the condom 10 on, the user 12 first steps through the waistband 40 so that both of the leg straps 41-A and 41-B extend between his two legs 60 and 62. The waistband 40 would then be pulled up to the waist 46 of the user 12 and the user 12 would then insert his penis (not illustrated) into the tubular sheath portion 18 and insert his scrotum (not illustrated) into the bag portion 26 as previously described.

While the invention has been described with a certain degree of particularity, it is manifest that many changes may be made in the details of construction and the arrangement of components without departing from the spirit and scope of this disclosure. It is understood that the invention is not limited to the embodiment set forth herein for the purposes of exemplification, but is to be limited only by the scope of the attached claim or claims, including the full range of equivalency to which each element thereof is entitled.

What is claimed is:

1. A condom for use by a male user, comprising:
    a protective section, said protective section comprised of a hollow tubular sheath portion connected to a hollow bag portion so that the hollow tubular sheath panion communicates with the hollow bag portion in order that the tubular sheath portion cover a penis of a user and the hollow bag portion cover a scrotum of the user,
    a second protective layer being provided with a first end and with an opposite second end, said second end being secured to an external surface of the tubular sheath portion, said first end being unattached to the tubular sheath portion and freely extendable to a proximal end of said tubular sheath portion, and
    a belt section being attached to the protective section to hold the protective section on the user.

2. A condom for use by a male user according to claim 1 wherein the tubular sheath portion is sealed on a distal end and is attached on the opposite proximal end to an anterior side of the bag portion.

3. A condom for use by a male user according to claim 2 wherein the bag portion is provided with an upward oriented opening for admitting the penis and scrotum of the user into the tubular sheath portion and the bag portion respectively, and said opening being provided with an elasticized peripheral edge to secure the bag portion to the scrotum.

4. A condom for use by a male user according to claim 3 wherein the belt section is further comprised of a waistband and at least one leg strap, each said leg strap being provided with a back end and an opposite front end, each said back end attaching to a back area of the waistband, each said front end attaching to the bag portion, and the bag portion attaching to a front area of the waistband.

5. A condom for use by a male user according to claim 4 wherein each said front end attaches to the bag portion at a posterior area on the peripheral edge, and an anterior area on the peripheral edge of the bag portion attaches to a front area of the waistband.

6. A condom for use by a male user according to claim 4 wherein two leg straps are provided, the back ends of each said leg strap being attached to the waistband so that the back ends are spaced apart.

7. A condom for use by a male user according to claim 2 wherein the second end of the second protective layer is secured to the external surface of the tubular sheath portion midway between the distal and proximal ends.

* * * * *